United States Patent [19]

Roessler et al.

[11] Patent Number: 5,176,671
[45] Date of Patent: Jan. 5, 1993

[54] FASTENING SYSTEM FOR DISPOSABLE DIAPER WITH DISPOSABILITY FEATURE

[75] Inventors: Thomas H. Roessler, Menasha; Bruce M. Siebers, Appleton; Robert L. Popp, Hortonville; Charles R. Fallen, Neenah, all of Wis.

[73] Assignee: Kimberly-Clark Corporation, Neenah, Wis.

[21] Appl. No.: 627,874

[22] Filed: Dec. 13, 1990

Related U.S. Application Data

[63] Continuation of Ser. No. 287,746, Dec. 20, 1988, abandoned.

[51] Int. Cl.5 .................. A61F 13/15; A61F 13/20
[52] U.S. Cl. ..................... 604/391; 604/386; 604/385.1
[58] Field of Search .................. 604/385.1, 386-391

[56] References Cited

U.S. PATENT DOCUMENTS

| | | | |
|---|---|---|---|
| 4,410,327 | 10/1983 | Buggaley | 604/391 |
| 4,773,906 | 9/1988 | Krushel | 604/397 |
| 4,869,724 | 9/1989 | Scripps | 604/391 |
| 4,994,054 | 2/1991 | Pigneul et al. | 604/391 |
| 5,019,065 | 5/1991 | Scripps | 604/391 X |
| 5,019,072 | 5/1991 | Polski | 604/389 |
| 5,019,073 | 5/1991 | Roessler et al. | 604/391 |

FOREIGN PATENT DOCUMENTS

| | | |
|---|---|---|
| 74625/74 | 4/1976 | Australia . |
| 0013463 | 7/1980 | European Pat. Off. ............ 604/391 |
| 319249A1 | 6/1989 | European Pat. Off. . |
| 321232A1 | 6/1989 | European Pat. Off. . |
| 321234A1 | 6/1989 | European Pat. Off. . |
| 324577A1 | 7/1989 | European Pat. Off. . |
| 324578A1 | 7/1989 | European Pat. Off. . |
| WO83/03754 | 11/1983 | PCT Int'l Appl. . |
| 1430747 | 4/1976 | United Kingdom ................ 604/391 |
| 2233876 | 1/1991 | United Kingdom ................ 604/391 |

*Primary Examiner*—David Isabella
*Assistant Examiner*—Elizabeth M. Burke
*Attorney, Agent, or Firm*—Paul Yee

[57] ABSTRACT

There is disclosed a disposable diaper in which the waistband is closed by a mechanical fastener. A second fastener means is included and positioned on the article to enable rolling or folding the garment after use and thereby secure it in a neat bundle for disposal. In the disclosed embodiments, the mechanical fastener is comprised of hook tabs at the rear waistband which engage a patch of loop material adhesively bonded on the front waistband. The second fastener means of the disclosed embodiments utilizes the tabs which engage a compatible component on the garment placed in the same half portion with the tabs. The disclosed species of the second (disposability) fastener means include: (1) tabs comprised of a hook component on one surface and loop component on the opposite surface thereof; or (2) tabs comprised of a hook component and a loop component on the outer surface in the same (rear) half of the garment; or (3) tabs comprised of a hook component and a loop component on the outer surface at the rear half of the cover in the region of the ears which is comprised of either the loop material mounted on the garment outer surface or is a non-woven material portion configured to function with the hook component and perform the secondary fastening function; or (4) tabs comprised of a hook component area and a pressure-sensitive adhesive area, the latter adhesively fastening the tabs to the rear half of the outer polymer cover sheet of the garment; or (5) tabs comprised of a hook component and transverse interlocking slots in the tabs, which link the ends of the rear waistband around the rolled garment to secure it for disposal.

26 Claims, 13 Drawing Sheets

FASTENING SYSTEM FOR DISPOSABLE DIAPER WITH DISPOSABILITY FEATURE

This is a continuation of copending application(s) Ser. No. 07/287,746 filed on Dec. 12, 20, 1988, now abandoned.

The invention relates to an absorbent article, such as a diaper, incontinent garment or the like, and more particularly to fastening systems for securing placement of the article on the body of the user, and subsequently for fastening the used article in a folded or rolled condition for disposal.

BACKGROUND OF THE INVENTION

In the prior art, various fastening systems have been employed for fastening the waistband of a disposable diaper around the waist of the wearer. The fastening device generally includes side tabs attached to the ears of the garment in the rear waistband. The rear waistband overlaps the front waistband as the article is placed on the body of the user and the tabs are fastened onto the front waistband portion holding the garment in snug encircling fashion on the torso. After the garment is soiled, it is removed by unfastening the tabs opening the waist.

Fastening systems heretofore in use have included adhesive fastening, such as shown, in U.S. Pat. Nos. 3,180,355; 3,630,201; 4,047,530; 4,049,001; 4,050,453 and French Patent 7,436,169. The fastening device generally comprises an adhesive tab attached to the outer (backing) sheet of the diaper at the rear portion and the active adhesive surface of the tab is stuck onto another portion of the backing sheet surface near the front portion thereby closing the diaper. The adhesive system for the primary fastening system of the waistband around the wearer is susceptible to contamination of either the adhesive tab surface or the cover surface to which the adhesive tab is applied. Recently, mechanical closure systems have been devised using hook (e.g. "mushroom") and loop (for example, Velcro ®) fasteners for closure of the waistband, such as is set forth by French Patent No. 2,594,650 and EP 0 276 970 A2. In a copending U.S. application, Ser. No. 089,660, filed Aug. 25, 1987, owned by the assignee of the present invention, a mechanical fastener system is disclosed for fastening the leg openings of the garment at its sides extending downwardly from the waistband to enclose the legs and seal the garment around the legs and provide neat and trim fit. This system utilized a mechanical fastener system comprised of a combination of snap elements and such snap elements are interspersed with hook and loop fastener segments.

SUMMARY OF THE INVENTION

The present invention provides a mechanical primary fastening system for a garment, such as a diaper, incontinent garment or the like, for closing the waistband around the user and which operates in combination therewith a secondary fastening system to securely seal a soiled garment after use in a rolled or folded condition for disposal.

The invention includes several embodiments in which the primary fastening plus fastening for disposability is provided in attachment tabs at one longitudinal end of the garment that cooperate with primary fastening zones in the opposite end portion of the garment and discrete secondary disposability zones in the same longitudinal half of the garment as the tabs, the tabs being normally attached to the ears in the rear portion of the garment, and the secondary disposability zones also being located on the rear portions, or, in particular, on the reverse side of the attachment tabs or on the rear half of the outer cover portion.

In one preferred form, the primary fastener system utilizes hook and loop fastener components, one of the components being a part of the attachment tabs at one longitudinal end of the garment and the other component is attached to the outer cover portion at the other longitudinal end of the garment for closing the waistband of the garment; and the secondary fastener system for disposal of the garment after use utilizes the attachment tabs which engage the discrete secondary disposability zones positioned in the same longitudinal half portion of the garment. Examples of these fasteners are disclosed hereinafter.

DETAILED DESCRIPTION OF THE INVENTION

Figure 1:
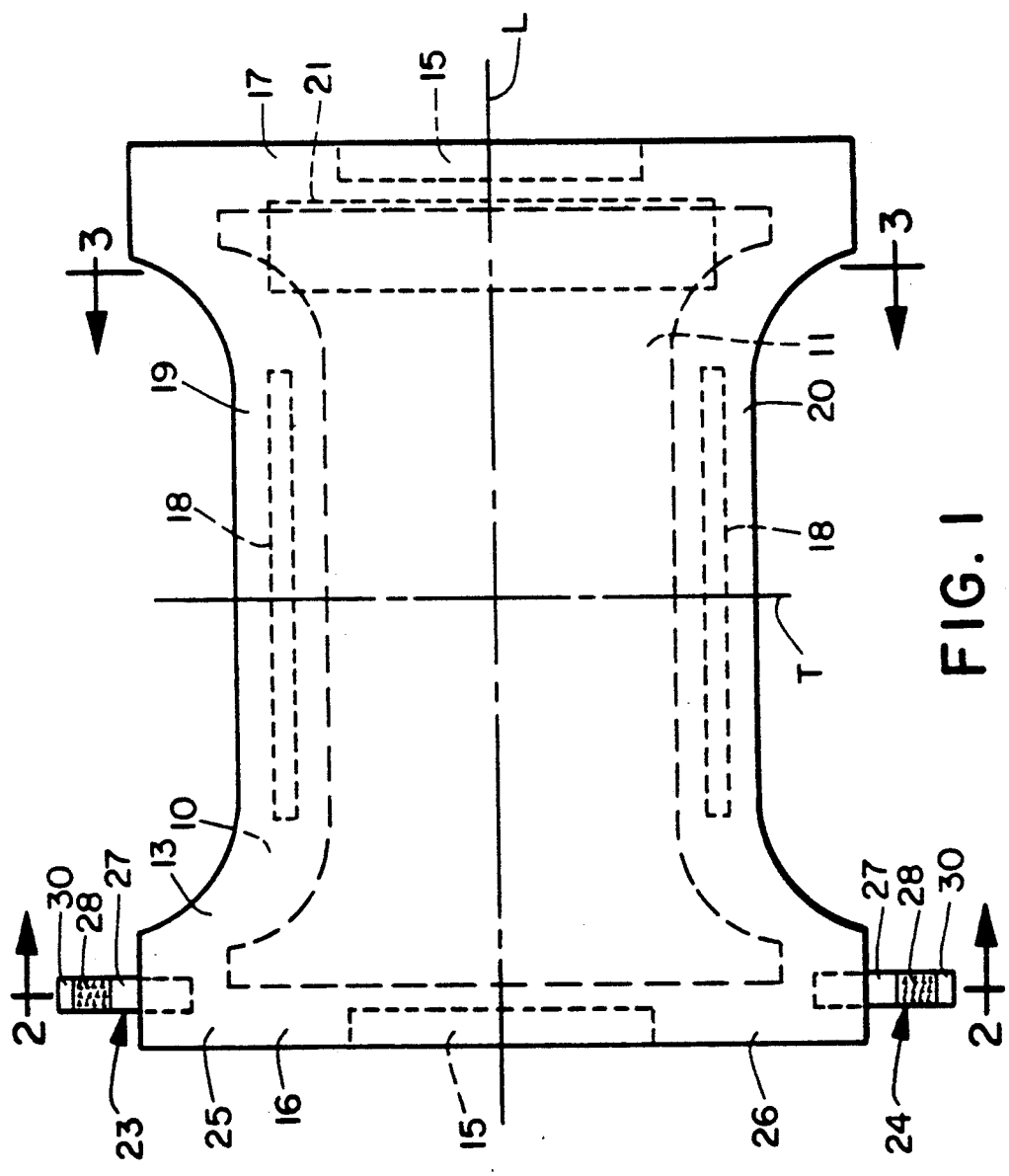
FIG. 1 is a top plan view of a disposable diaper constructed according to a first embodiment of the invention.

The absorbent article illustrated by the embodiments shown on the drawings utilizes a first fastener means of the mechanical type positioned at one of the longitudinal ends of the garment which comprise one waistband portion of the article. The other cooperating waistband portion is at the opposite longitudinal end of the garment; the two waistband portions encircling the waist of the user in overlapping fashion. The mechanical type fastener illustrated includes two cooperating components mounted on the waistband portions that interengage one another in the overlapping of the waistband portions to releasably fasten the waistband in an adjusted, snug fit on the wearer. One component is a hook style swatch or tab and the second component is a loop style patch.

In the present invention, a second fastener means is included and positioned on the article to enable rolling or folding the absorbent article after use into a neat bundle for subsequent handling and disposal. This second fastener means may utilize the one component placement on the waistband of the first fastener and combines with it a separate and compatible component in the same longitudinal half of the article such that two components of the second fastener means are engaged to hold the rolled or folded article in its disposability condition.

There are several preferred forms of the invention shown in the attached drawings. In describing the several embodiments, the same or similar parts of the article are identified by the same reference numeral.

FIRST EMBODIMENT

Referring to FIGS. 1-4, an absorbent article is constructed which has a primary mechanical fastener for the waistband of the article and a secondary fastener providing the disposability feature. The article includes an elongated backsheet 10 constructed of a layer of 1 mil polyethylene and $TiO_2$ filler which is overlaid with absorbent body 11, such as an absorbent body comprising 78% airlaid cellulose fiber and 11% hydrogel, enclosed in a 9% tissue wrap 12. The absorbent body has a density on the order of 0.12 grams per cubic centimeter. The absorbent body 11 is overlaid with a liquid permeable topsheet 13 corresponding in shape to backsheet 10. An example of the topsheet is a 0.75 ounce per square yard polypropylene spunbond material. The backsheet 10 and topsheet 13 are fastened together peripherally by a spray application of adhesive 14, such as National 70-3016 adhesive. The tissue wrap 12 is likewise adhesively attached to the inside of backsheet 10.

A suitable hook material may, for example, be produced from a process of continuous injection molding of a polymeric material, such as a polypropylene copolymer. It has been determined that the proper stiffness of the material is obtained from the copolymer having flexural modules of 70,000 -120,000 psi and shore hardness value within the range of about D-40 to D-80, preferably about D-61.

The base strata of the hook material is fabricated onto the surface of the tab 30 by adhesive, heat-bonding or sonic-welding to provide the J-shaped hooks in a configuration facing outwardly of the tab structure. The hooks are tapered base to top with an alternating hook design. A specific example of a suitable hook is the HTH #707 available from Velcro U.S.A. The overall thickness (caliper) of the hook material is in the range of 0.035 to 0.050 inch, and preferably about 0.045 inch. The hooks are attached to a base film which is in the range of 0.005 to 0.025 inch thick, preferably a thickness in the range of about 0.008 to 0.010 inch. The hook density on the base is within the range of 440 to 1040 hooks per square inch; preferably a hook density of about 740 hooks per square inch, as a particular example, hook material having a row density within the range of about 20-60 rows to the lineal inch of width, preferably a row density of about 40 rows per lineal inch. The material used may be clear or opaque with selected color of the material.

A representative loop component of the hook and loop fastener is a fabric material of raised loop construction in which the fabric is stabilized (loops are erect from the fabric's base) through napping. Additionally, the loop material may be thermoset to impart other properties, such as is set forth in U.S. Pat. No. 3,475,926 issued Nov. 4, 1969 to J. Ruckstuhl and 3,090,097 issued May 21, 1963 to J. Ruckstuhl.

Preferably, a material of polyolefin-based fibers or other synthetic fibers is used; an example of the fabric being a tricot polyester. More specifically, polyethylene terephthalate (PET) fiber mix in which about 15-35% of the fabric yarns are yarns composed of 1-15 filaments with the yarn having a denier within the range of about 15-30d, and about 65-85% of the fabric yarns are yarns having about 10-30 filaments per yarn and having a yarn denier within the range of about 30-50d comprises the fibers used in the fabric. Two bar warp knit construction is preferred in which courses are in the range 21-41 per inch and wales are in the range 26-46 per inch. The surface of the fabric is napped. The thickness caliper is within the range of about 0.01 to 0.04 inch, the preferred caliper being about 0.035 inch. The basis weight of the fabric is in the range of about 1.0 to 3.0 ounces per square yard; the preferred basis weight being about 1.6 ounces per square yard. The fabric is printable or decoratable directly, or in the alternative may be laminated over a predecorated film base, whereby a print pattern shows through the loop material. Loop material is applied onto the front waistband portion 17 in a patch or swatch 21 with the loops erect and facing outwardly from the face of the backsheet 10. The extent of patch 21 may be varied and may take one of several geometric shapes, such as rectangular, irregular shape, diamond, triangle, circle, oval, chevron or the like. The loop material may also be configured as a plurality of patches. The plural patches (two or more) form a landing zone for the hook tabs which are composed of multiple, separate sections. The variation of shape or configuration of multiple patches will lend itself to desired function and size for fastening the waistband about the various sizes of users.

Waist elastic members 15 (shown schematically on FIG. 1) are attached along the opposite waistband portions 16 and 17 at the opposite longitudinal ends of the article. Preferably, the members 15 are at the outside margins of the waistbands 16 and 17, respectively. The elastic members are arranged to gather and shirr the waistbands 16 and 17 of the garment to provide a seal about the waist of the wearer. Also, leg elastic members 18 are attached to the opposite side margins 19 and 20 of the article and arranged to gather and shirr these side margins to provide seals about the legs of the wearer.

A first fastener means is provided on the garment comprising a fastening patch of loop material 21. The loop material 21 is one of the two components of the primary fastener means, and it interengages a second component in the form of hook materials, to be presently described. Loop material 21 may comprise a woven or nonwoven material. Preferably, the loop material is a Guilford warp knit fabric, number 19902, 1.57 ounces per square yard, made from polyester fiber. Loop patch 21 is, for example, attached by adhesive 22 (FIG. 3) to the outside surface of backsheet 10 just below and interiorly of the elastic member at waistband 17. Patch 21 may alternatively extend to the terminal edge of the waistband. The loop material patch 21 may be adhesively fastened using National 70-3016 hot melt adhesive available from National Starch Company, in Bridgewater, New Jersey. In normal use, waistband 17 is disposed at the front of the garment article and waistband 16 is the rear portion which includes the ear portions 25 and 26. Waistband 16 wraps around the back of the torso and overlaps onto the front waistband 17; however, the garment may be constructed for encircling the waist in the reverse order. For the sake of description and illustration only, the front and rear waistbands 17 and 16, respectively, are identified in accordance with the conventional arrangement and use of the garment.

At the end portion of the article opposite the patch 21, [in this case, at the rear waistband 16] two fastener tabs 23 and 24 are attached securely to the backsheet to extend outwardly from the opposite ear portions 25 and 26, (FIG. 1), respectively, of the garment. Tabs 23 and 24 are each constructed of a tape 27 composed, for example, of a plastic film substrate, such as a 4.5 mil polypropylene having $TiO_2$ filler. As illustrated in FIG. 2, the tabs each have end segments of the film sandwiched between the backsheet 10 and topsheet 13 in the opposite ear portions 25 and 26 along the sides of the article and the film substrate is attached thereat by a hot melt adhesive, such as National 70-3016 hot melt adhesive. The secured overlap of the tape 27 with backsheet 10 and topsheet 13 is approximately 1.0 inch measured inwardly from the margin of the ear portion; however, the overlap may be from 0.25 to 4.0 inches. A fastener component, such as a region of hook material 28, is incorporated onto the film substrate to face upwardly in the direction of top sheet 13. In the illustrated embodiment, the hook material 28 is attached to the film substrate with hot melt adhesive 29 (National 70-3016 being a satisfactory adhesive for this purpose). In an alternative embodiment, the hook material may be integrally formed with the film substrate. Hook material 28 may comprise Velcro ® hook "style 15" and may be composed of a polypropylene, such as Telcar 102 polypropylene distributed by Teknor Apex Co. of Pawtucket, Rhode Island, or Ferro polypropylene 9004N distributed by Horizon Polymers of Houston, Texas. A finger tab portion 30 is exposed at the free outboard end of the attaching tape 27 for ease in grasping the tab and releasing the hook component once it is affixed to the loop component.

Figure 4:
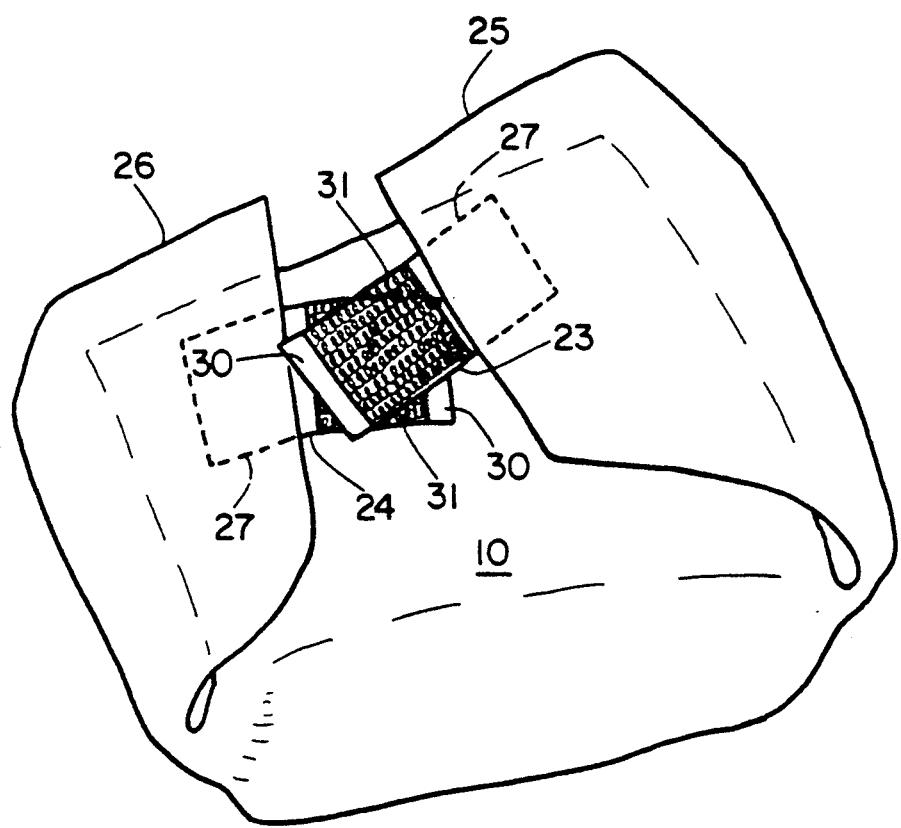
FIG. 4 is a perspective view of the diaper of FIG. 1 folded and fastened for disposal.

A second fastener means is provided by attaching a patch 31 of loop component material to the opposite, underside of each of the tabs 23 and 24 as is shown on FIGS. 2 and 4. The loop patch 31 may be comprised of Guilford warp knit fabric 19902 of polyester fiber. Loop patch 31 is integrated with the polypropylene film substrate by hot melt adhesive 32, such as National 70-3016. In another embodiment of the invention, loop patch 31 may comprise a fibrous nonwoven loop material.

The garment is placed on the body of the wearer and front waistband 17 is overlapped by rear waistband 16 bringing the ear portions toward each other to a firm or snug fit. The hook material 28 on tabs 23 and 24 are pressed onto and engage the loop material of patch 21 facing outwardly on the backsheet at the front waistband mid-portion. The primary hook and loop fastener of the type described for closing the waistband and holding it in service about the wearer should have properties of shear force in the range of 6.6–20 psi, and peel force in the range of 200–1200 grams per lineal inch of transverse width. A preferred peel force value is within the range of about 400–600 grams per inch width.

"Shear" is determined according to ASTM Designation: D3654-82, "Standard Test Method for Holding Power of Pressure-Sensitive Tapes", which is incorporated herein by reference, and subject to the following modifications: In relation to the test, the closure is placed under an increasing load. The system being tested is a hook and loop closure system. (See 1. Scope). The apparatus should include an "INSTRON" or equivalent continuous rate of extension (CRE) tensile tester. (See 3. Apparatus). In carrying out the procedure (See 6. Procedure), test direction of the materials should be noted. The test materials are rolled five cycles (1 sq. in.), where one cycle equals once in each direction. The hook material is clamped into the lower jaw of the Instron tensile tester. The engaged system (hook and loop) is pulled until failure. In doing the calculations (See 10. Calculations), the peak load is determined and recorded in grams.

"Peel" is determined according to ASTM Designation: D1876-72, "Standard Test Methods for Peel Resistance of Adhesives (T-Peel Test)", which is incorporated herein by reference, and subject to the following modifications:

4.1 No test panels are used; hook and loop materials are directly engaged and are not mounted on any other substrate unless specified. Test direction of the material should be noted. No panels are used. The engaged test materials are rolled five cycles; where one cycle equals once in each direction. The hook material is clamped into the upper jaw and the loop material is clamped into the lower jaw.

In a suitable hook and loop fastening system, the fastener has a total peel resistance of at least about 150 gm. and preferably has a total peel resistance of at least about 400 gm. The total shear force resistance is at least about 750 gm. and preferably is at least about 1000 gm. It should be readily recognized that a suitable fastening system will include a selected balance between the property of total peel resistance and the property of total shear force resistance. For example, a system with the lower values of peel resistance could be more suitable if the system also exhibited a higher total shear force resistance.

For the purposes of the present description, the total peel resistance value corresponds to the peel force determined in accordance with ASTM D1876-72 multiplied by the transverse width of engagement between the hook material and the loop material employed in the particular fastening system. Similarly, the total shear force resistance value corresponds to the shear stress determined in accordance with ASTM D3654-82 multiplied by the area of engagement between the hook material and loop material of the fastening system.

Referring to FIG. 4, the garment is disposed of after use by folding or rolling it inwardly, then overlapping tabs 23 onto 24 so that the loop patch 31 on the one (upper) side of the lowermost tab of the two is engaged by the hooks 28 on the (lowermost) side of the upper tape 23 of the two tapes, as shown. Since, in the embodiment shown, both tabs 23 and 24 have loop patch 31 on their one surface opposite from the hook material 28, the tabs 23 and 24 may be overlapped in reverse order from that shown on FIG. 4, depending upon user preference.

The hook and loop fastener of this secondary fastening system preferably should have properties of minimum shear of about 200 grams per square inch, and minimum peel of about 75 grams per lineal inch width of tab. The shear and peel properties of the secondary fastening means may be less than the primary fastening means because in the rolled disposal state, the garment is not subjected to the same forces as that offered by the wearer.

A preferred example of the absorbent article of this embodiment is a disposable diaper, as shown on FIGS. 1-4. The dimensions for the primary and secondary fastening systems for absorbent articles are the following:

posed in the same longitudinal half of the diaper with ears 25 and 26. National 70-3016 hot melt adhesive may be used to apply the patch 35 to the polymer backsheet. The patch 35 is constructed of a loop material, an example of which is Guilford warp knit fabric 19902 made of polyester. Patch 35 is placed such that it is centered on the longitudinal axis L and is generally in the back half of the diaper, that is the half of the diaper left of the transverse center line T on FIG. 5.

Figure 5:
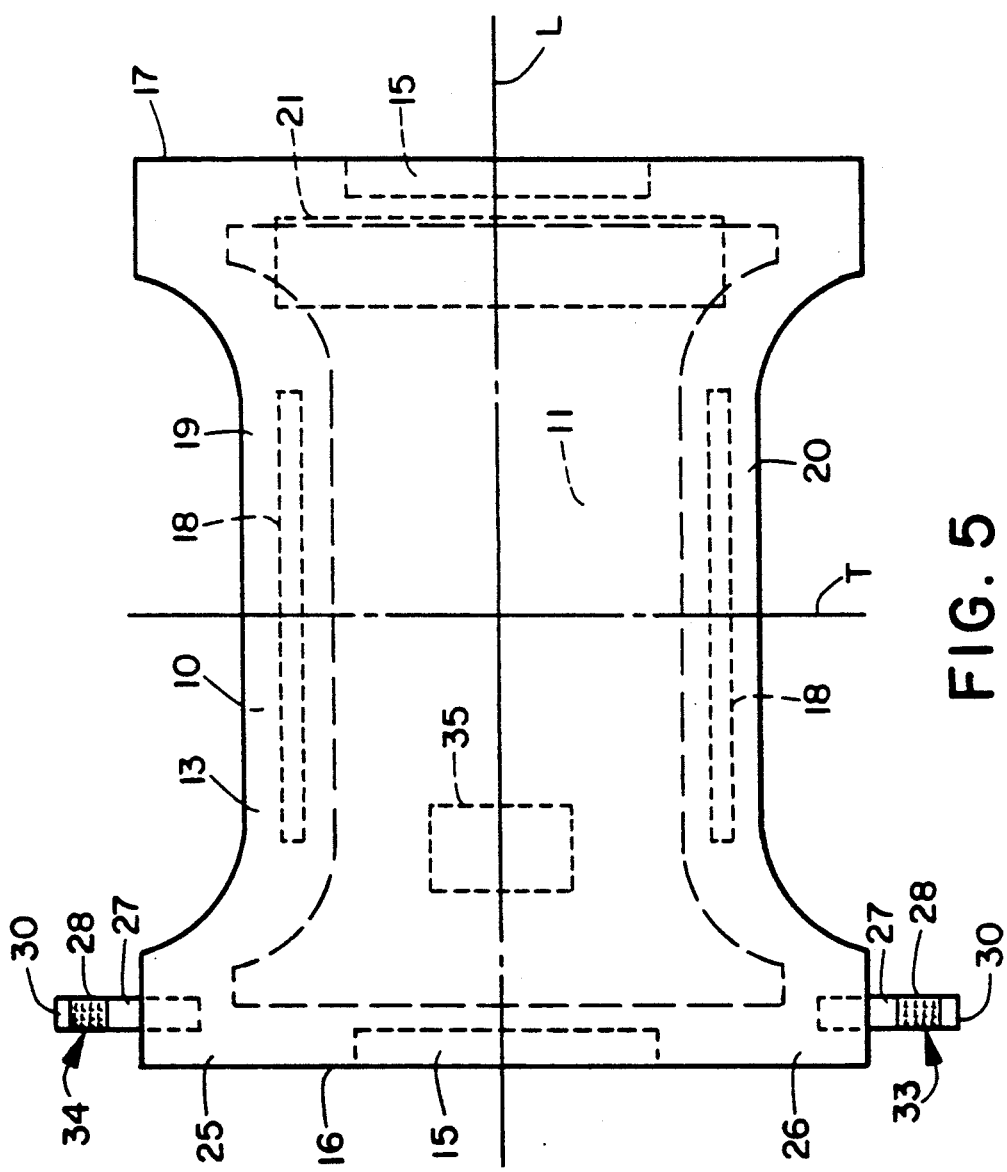
FIG. 5 is a top plan view of a disposable diaper constructed according to a second embodiment of the invention.
Figure 6:
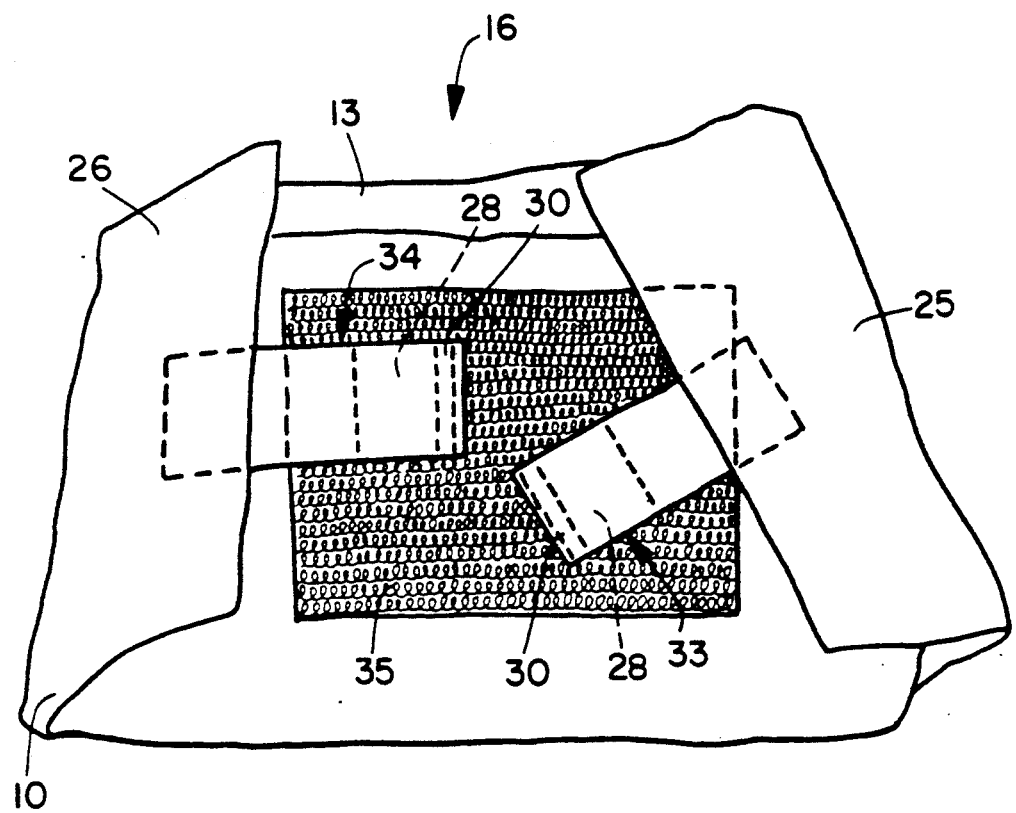
FIG. 6 is a perspective view of the diaper of FIG. 5 folded and fastened for disposal.

Referring to FIG. 6, the garment may be disposed of after use by folding or rolling it inwardly from the front waistband 17 beyond the transverse center T (FIG. 5) such that the patch 35 is generally disposed between ear portions 25 and 26 and facing outwardly. The tabs 33 and 34, which were part of the primary fastening system, are brought inwardly and toward each other so that the hook material 28 of each overlies the loop material of patch 35 and then pressed into engagement. The hooks 28 of tabs 33 and 34 attach to loops of patch 35 and form a secure secondary fastener holding the used garment in its rolled or folded condition for convenient disposal.

As was earlier mentioned, the hook and loop fastener of this secondary fastening system should have properties in shear of about 200 grams per square inch (minimum), and peel about 75 grams per lineal inch width (minimum). These properties of shear and peel may be

| Part Name | No. | Range Width | Range Length | Preferred Dimensions For Medium Diaper Width | Length |
|---|---|---|---|---|---|
| Loop Patch | 21 | .5-5 in. | 4-14 in. | 1.75 in. | 9 in. |
| Fastening Tape | 27 | .25-4 in. | 0.75-6 in. | 1 in. | 3 in. |
| Hook Material | 28 | .25-4 in. | .1-4 in. | 1 in. | 0.5 in. |
| Disposal Loop Patch | 31 | .25-4 in. | .1-4 in. | 1 in. | 0.5 in. |
| Finger Tab | 30 | .25-4 in. | 0-5 in. | 1 in. | 0.19 in. |

SECOND EMBODIMENT

Referring to FIGS. 5 and 6, there is illustrated a second embodiment of the invention utilizing the secondary fastener means to secure the garment for disposal after use.

Figure 2:
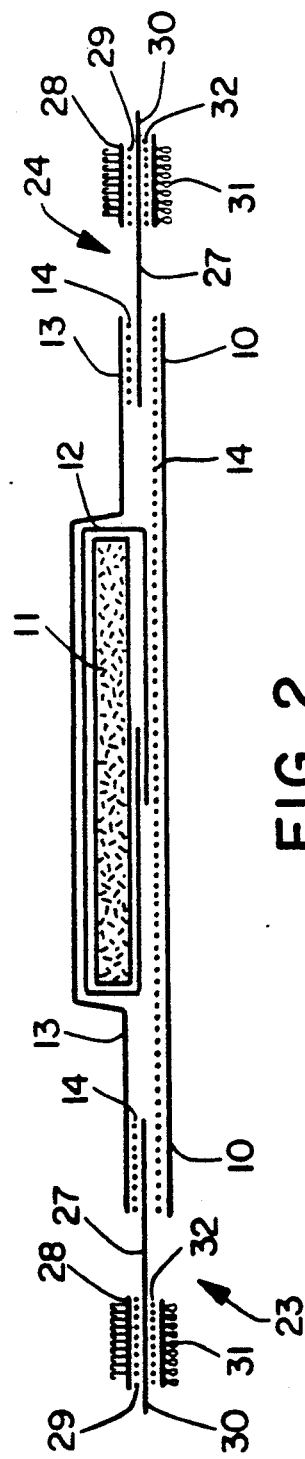
FIG. 2 is a sectional view (somewhat schematic) taken along line 2—2 on FIG. 1.
Figure 3:
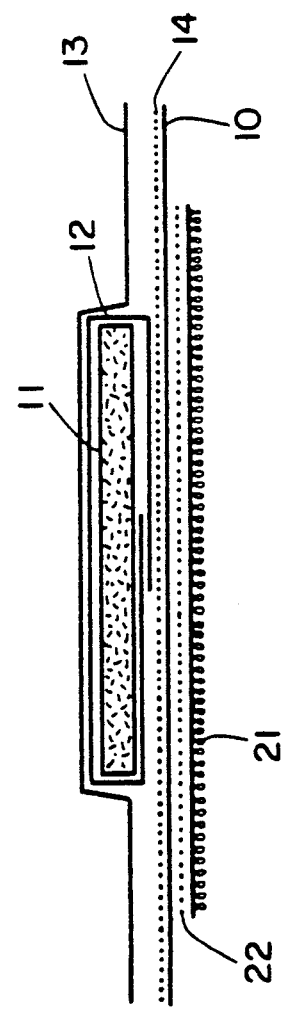
FIG. 3 is a sectional elevational view (somewhat schematic) taken along line 3—3 on FIG. 1.

The article illustrated comprises a disposal diaper constructed similar to FIGS. 1-3. The liquid impermeable backsheet 10 and liquid permeable topsheet 13 have an absorbent body 11 enclosed by tissue wrap 12 sandwiched therebetween. The sheets 10 and 13 are attached by adhesive 14.

Loop material 21 in the form of an elongated patch is placed at the front waistband 17. The attachment tabs 33 and 34 are each constructed from tape 27, described earlier herein, have one inboard end disposed between backsheet 10 and topsheet 13 and adhesively attached at the margin of ear portions 25 and 26. The outboard portion of the tape 27 is provided with a hook material 28 attached to the tape and facing upwardly on FIG. 5.

A second loop material patch 35 is adhesively attached to the backsheet 10 facing outwardly and disposed less than that employed in the primary fastening means such as the tabs 33 and 34 are seated on patch 21 for securing the garment around the waist of a wearer. The forces applied against the primary fastening of the waistband are greater while in service on the wearer; whereas, once rolled for disposal the garment needs meet only the forces tending to open up or unroll from the disposal form.

A preferred example of the absorbent article of this second embodiment is a disposable diaper, such as shown on FIGS. 5 and 6. The dimensions for the components of the primary and secondary fastening means are the following:

| Part Name | No. | Range Width | Range Length | Preferred Dimensions For Medium Diaper Width | Length |
|---|---|---|---|---|---|
| Loop Patch | 21 | .5-5 in. | 4-14 in. | 1.75 in. | 9 in. |
| Fastening Tape | 27 | .25-4 in. | 1-6 in. | 1 in. | 3 in. |
| Hook Material | 28 | .25-4 in. | .1-4 in. | 1 in. | .5 in. |
| Disposal Loop Patch | 35 | .25-5 in. | .25-5 in. | 2.5 in. | 3 in. |

THIRD EMBODIMENT

Figure 7:
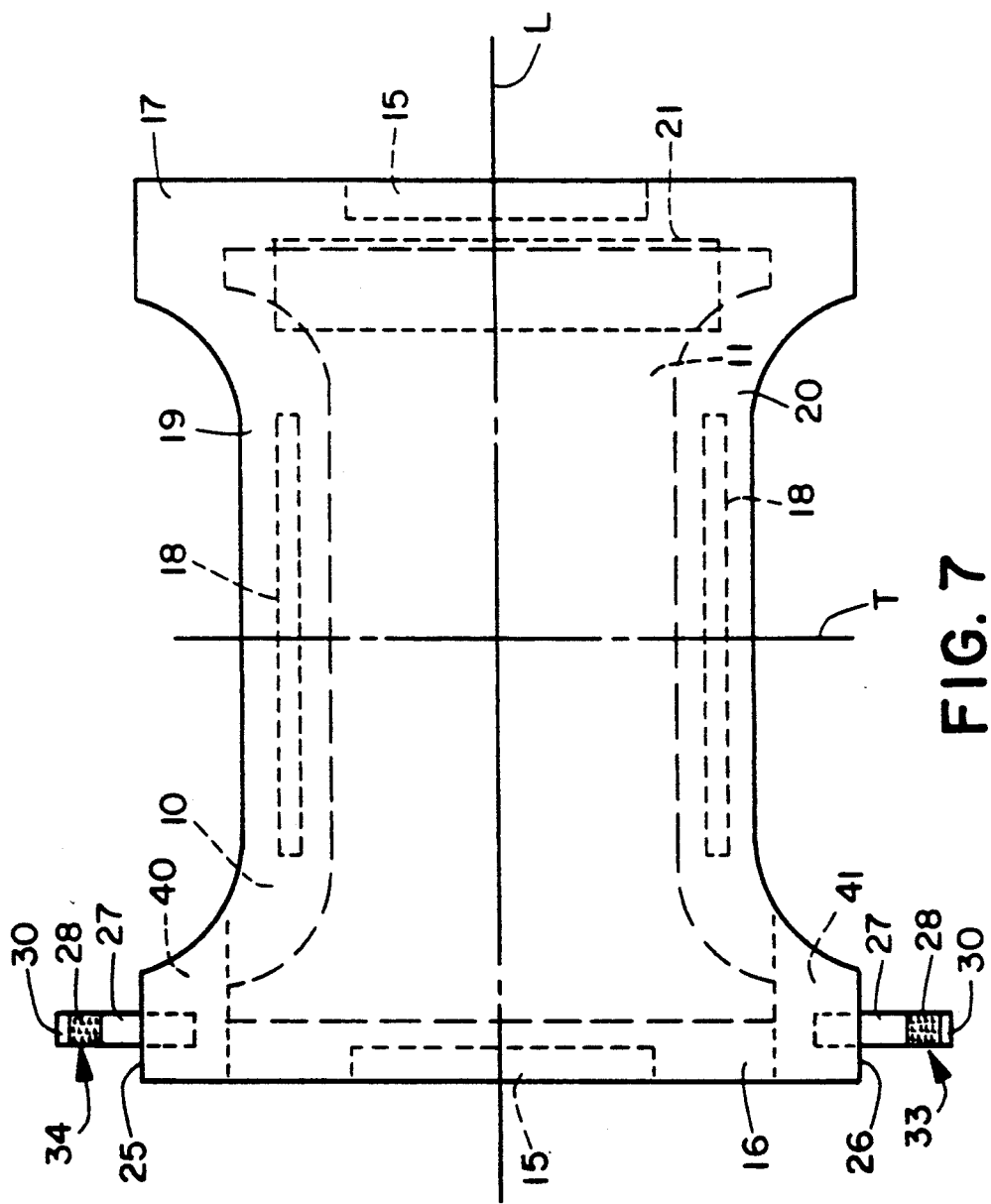
FIG. 7 is a top plan view of a disposable diaper constructed according to a third embodiment of the invention.
Figure 8:
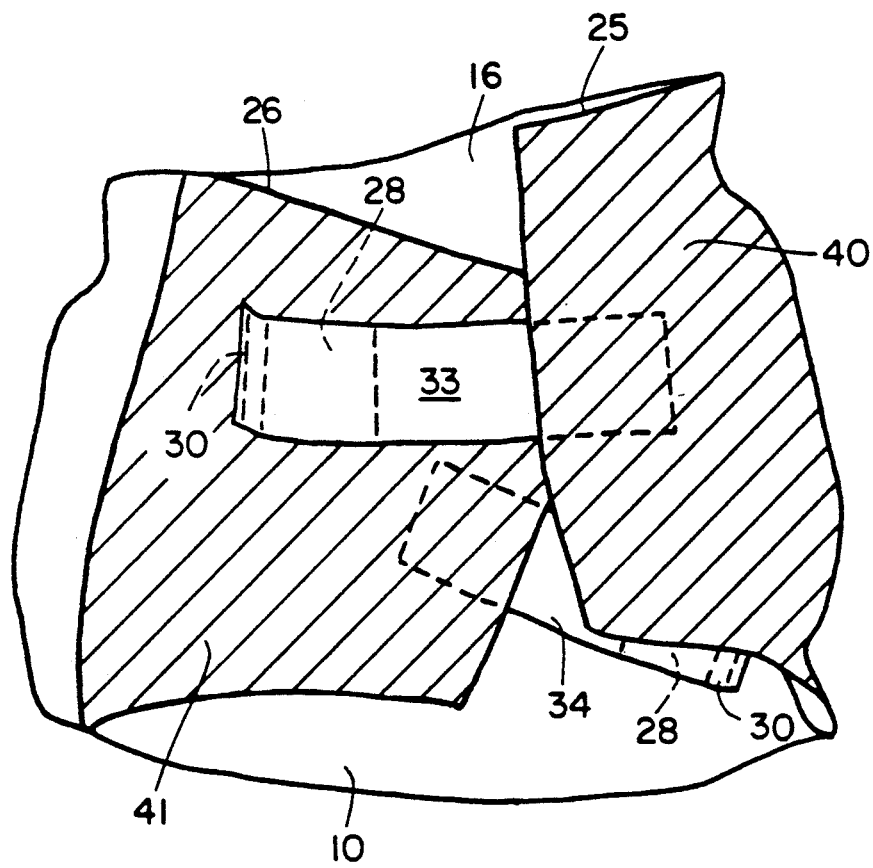
FIG. 8 is a perspective view of the diaper of FIG. 7 folded and fastened for disposal.

A further embodiment is shown on FIGS. 7 and 8 in which a different form of secondary fastener means is utilized to secure the rolled garment for disposal after use.

On FIG. 7, the absorbent article comprises a disposable diaper having a liquid impermeable backsheet 10 and liquid permeable topsheet 13. An absorbent body 11 enclosed in tissue wrap 12 is placed between sheets 10 and 13 which are adhesively attached to each other in the same manner as disclosed for FIGS. 1-3. Loop material is placed at front waistband 17 as patch 21 centered on the axis L and adhesively attached onto the outer surface of backsheet 10, as previously described. Attachment tabs 33 and 34 are constructed and attached to the ear portions of the article along the outer margins thereof at the rear waistband 16 in the manner previously described.

In the construction according to this embodiment, two disposal patches 40 and 41 of the loop material are adhered to the outside surface of backsheet 10 at the ear portions 25 and 26. For ease of illustration, the area of the patches 40 and 41 are schematically illustrated on FIGS. 7 and 8 by cross-hatching. Patches 40 and 41 may be of the same size, but are mirror images of each other. The loop material is by example a Guilford warp knit fabric 19902 made of polyester. Patches 40 and 41 are each adhered to the outer surface of polymer backsheet 10 at the respective ears 25 and 26 by hot melt adhesive, e.g. National's 70-3016. The hook tabs 33 and 34 are constructed in the manner previously described.

The garment is secured around the waist and fastened by the first fastening means whereby the hook tabs 33 and 34 along the rear waistband 16 overlap with and fasten onto the patch 21 of loop material at the front waistband. After use, the waistband is opened and the soiled garment may be rolled or folded inwardly, as before, by rolling from the front waistband 17 toward the rear waistband beyond the center, i.e. beyond transverse center line T. Next, the ear portions are brought inwardly along with their attached hook tabs. As shown on FIG. 8, one of the tabs, such as 33, may lie under the ear portion 25, whereas hook tab 34 is brought over and onto patch 41 of loop material on the opposite ear portion 26. In this arrangement, only one hook tab attached on the one ear portion need be attached to loop material of the opposite ear portion to secure the garment in its rolled state for disposal.

The patches 40 and 41 of this construction may be a nonwoven fibrous material, such as a polymeric nonwoven material of a type which will produce proper shear and peel properties of the secondary fastening system for this embodiment of the invention, as was earlier described. In this regard, the fastening properties of either the warp knit polyester fabric patch or nonwoven material disclosed which is used in conjunction with the hook-style of the tabs 33 and 34, disclosed earlier, are on the order of a shear (minimum) value of 200 grams per square inch and peel (minimum) value of 75 grams per inch of width.

As another variable, such non-woven material may be used over a substantially greater portion of the backsheet surface or may be used in place of the backsheet to provide the needed landing area for the hook tabs 33 and 34 in providing the secondary fastening means forming the rolled, disposable condition of the garment after use. The landing area for the secondary fastening system in such construction should comprise nonwoven fabric that is looped or fluffy such that the aforementioned shear minimum of 200 grams per square inch and peel minimum of 75 grams per inch width are provided.

As a preferred example of the absorbent article of this third embodiment of invention, a disposable diaper is constructed according to FIGS. 7 and 8 wherein dimensions for the fastening elements are the following:

| Part Name | No. | Range Width | Range Length | Preferred Dimensions For Medium Diaper Width | Length |
| --- | --- | --- | --- | --- | --- |
| Loop Patch | 21 | .5–5 in. | 4–14 in. | 1.75 in. | 9 in. |
| Fastening Tape | 27 | .25–4 in. | 1–6 in. | 1 in. | 3 in. |
| Hook Material | 28 | .25–4 in. | .1–4 in. | 1 in. | .5 in. |
| Disp. Loop Patch | 40,41 | .5–5 in. | .5–10 in. | 4 in. | 3 in. |

FOURTH EMBODIMENT

With reference to FIGS. 9-13, a fourth embodiment of the invention is shown in which another form of secondary fastener means is utilized to secure the rolled, used garment for disposal.

Figure 9:
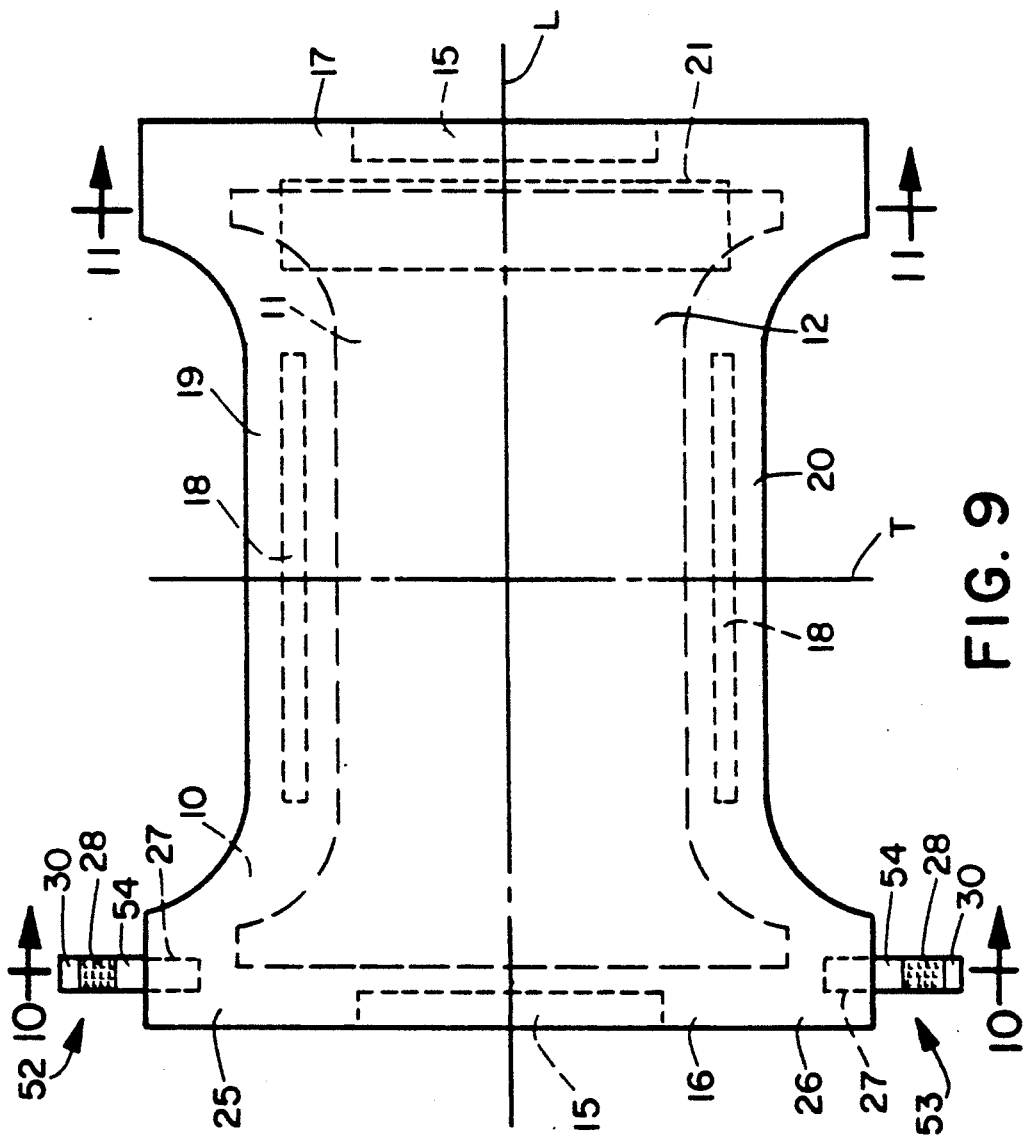
FIG. 9 is a top plan view of a disposable diaper constructed according to a fourth embodiment of the invention.
Figure 10:
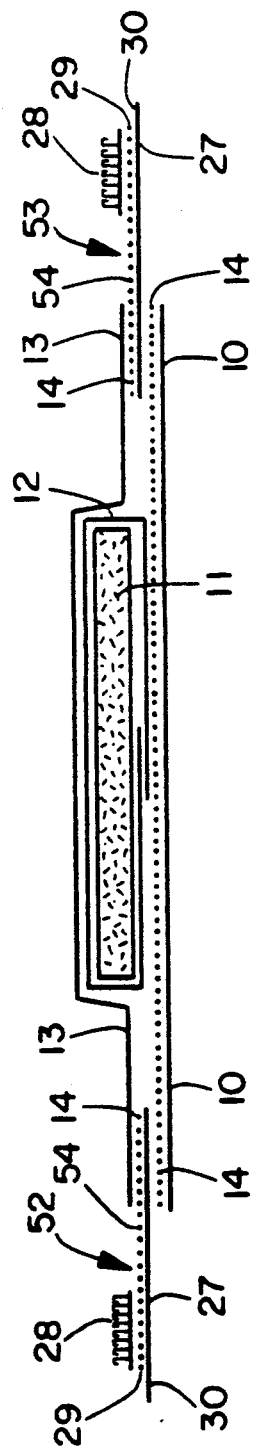
FIG. 10 is a sectional view (somewhat schematic) taken along line 10—10 on FIG. 9.
Figure 11:
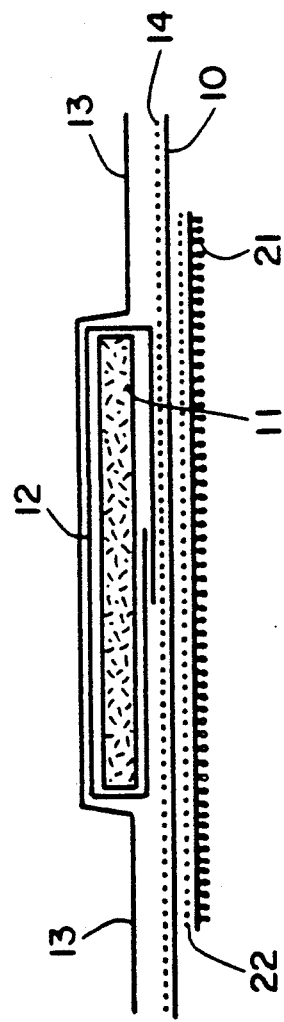
FIG. 11 is a sectional elevational view (somewhat schematic) taken along line 11—11 on FIG. 9.

On FIG. 9, a disposal diaper is shown, which is constructed generally much as the diaper article described and shown on FIGS. 1-3. This diaper of FIGS. 9-13 differs in that it has a mechanical fastener as the primary fastening means and a pressure-sensitive adhesive tape fastener as the secondary fastening means to secure the rolled diaper in disposable form.

The absorbent article includes the plastic backsheet 10, a liquid permeable topsheet 13 facing the backsheet and an absorbent body 11 wrapped in tissue wrap 12 disposed between backsheet 10 and topsheet 13. The tissue wrap is attached to the inner surface of backsheet 10 by adhesive. Waist elastic members 15 are attached at the back and front waistband margins 16 and 17, respectively, and are arranged to gather and shirr the waistband of the garment to seal about the waist of the wearer. Similarly, leg elastic members 18 attached alongside margins 19 and 20 are configured to gather and shirr the sides of the garment to form seals about the leg of the wearer.

A fastening zone for the primary fastening system comprises patch 21 attached on the outer surface of backsheet 10 just below the front waistband 17 using an adhesive, such as National 70-3016 hot melt adhesive. The patch 21 is centered across the longitudinal center axis L of the diaper. The patch fabric comprises, as one example, a Guilford warp knit fabric 19902 made 1.57 ounce per square yard basis weight of polyester fiber.

Two fastening tabs 52 and 53 are connected to the rear waistband 16 of the article at the lateral margins of the side ear portions 25 and 26. The attachment tabs 52 and 53 each comprise a tape of film substrate 27, such as 4.5 mil polypropylene plus TiO$_2$. As shown on FIG. 10, film tape 27 is attached between the topsheet 13 and backsheet 10 by adhesive 14, such as National 70-3016 hot melt adhesive. A hook tab 28 is attached to an outboard portion of tape film 27 by adhesive, such as the aforementioned National 70-3016 hot melt adhesive, placing the hook material adjacent the free end of the substrate. The outer portion of the tab is not adhesively coated and serves as finger tab portion 30. The hook material, by way of example, is Velcro hook style 15, made of injection molded Ferro polypropylene 9004-N. The span regions between hooks 28 and the margin of the diaper ear (areas 54) include a pressure-sensitive adhesive layer on the inwardly facing surface (next to topsheet 13) of the tape substrate. The adhesive surfaces 54 of the substrate tabs 52 and 53 provide for the secondary fastening means by which the adhesive layers 54 are attached to the outer cover of the diaper, i.e. the outer surface of plastic backsheet 10.

In another embodiment of the invention, each of the fastening tabs may be constructed from a commercially available strip of adhesive tape material which includes a pre-applied layer of pressure-sensitive adhesive located on one major surface thereof. Suitable adhesive tape material may, for example, be obtained from 3M Company, St. Paul, Minnesota. The pre-applied adhesive layer serves multiple purposes. First, the adhesive can be used to attach the hook tab portion to the fastening tab. Second, the pre-applied adhesive serves as the pressure-sensitive adhesive layer in span regions 54. With this arrangement, the finger tab can be produced by folding a section of the distal end of the fastening tab back on itself, adhesive side against adhesive side. The folded-over section thereby provides an adhesive-free region which can be readily grasped by the user's fingers.

The peel adhesion force value of about 11.7N, or greater, should be provided by the tabs 52 and 53 at their surfaces 54. The peel force values are determined with a one inch wide adhesive tape tab in accordance with Pressure Sensitive Tape Council procedure PSTC-1 (see ASTM-D3330), modified such that the one inch wide adhesive tape tab under test is peeled directly from a substrate composed of the selected material, in this case the plastic backsheet 10.

In the standard PSTC-1 test procedure, the test sample of adhesive tape is peeled at a peel angle of 180° from a steel block substrate measuring 2.5 inches wide and 6 inches long. In the procedure modified for the purposes of the present invention, both longitudinal ends of a 2.5 inch×6 inch sample of the selected reinforcement layer are bonded to the steel block over an area measuring 1 inch×2.5 inches, leaving an unbonded intermediate region which measures 4 inches×2.5 inches. A piece of fluff pad material measuring 2.5 inches×2.5 inches and having a basis weight of 800 grams per square meter is interposed between the steel block and the intermediate region of the reinforcement layer material to better simulate actual conditions on an absorbent article. The piece of fluff pad is held in place by friction, and the intermediate region is the target test zone against which the test tape is adhesively connected. The 180° peel separation rate is set at 18 cm./sec., and the dwell time between adhering the tape tab to the test zone and peeling away the tape tab is less than 10 minutes. Peel force values are recorded each 100 microseconds during the separation. Suitable test equipment is available form MTS Systems Corporation, Minneapolis, Minneapolis.

Figure 12:
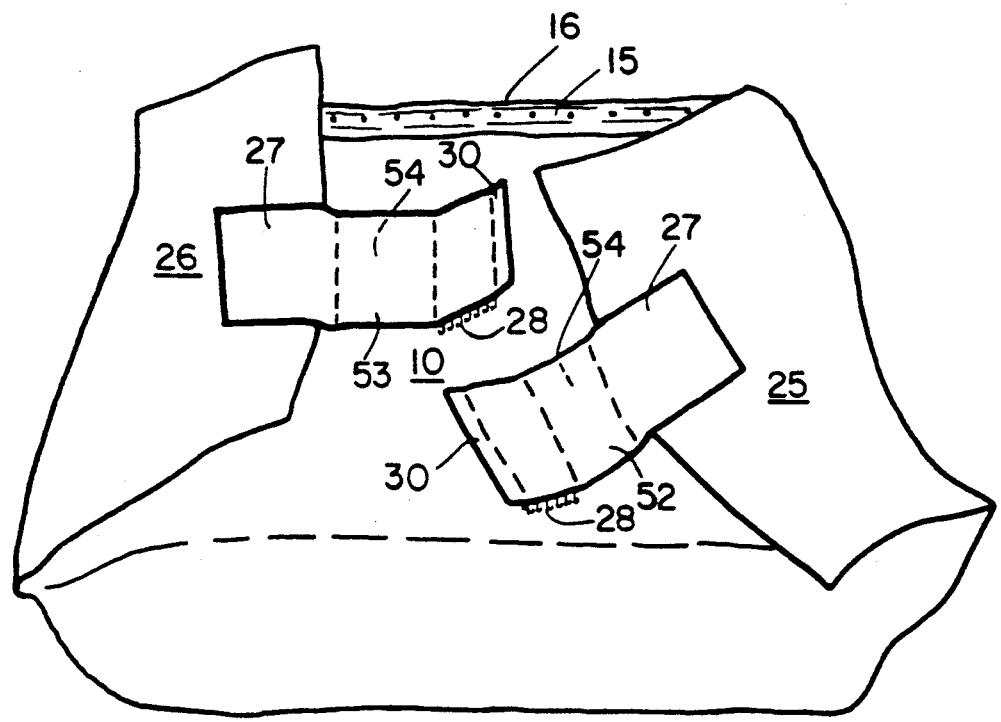
FIG. 12 is a perspective front view of the diaper of FIG. 9 folded and fastened for disposal.
Figure 13:
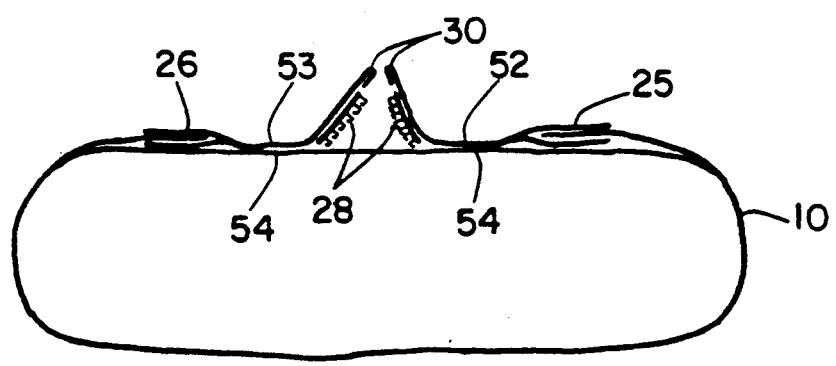
FIG. 13 is an end view in (part schematic) of the diaper of FIG. 12 which illustrates the secondary fastener of this embodiment in use to hold the folded diaper for disposal.

Referring to FIGS. 12 and 13, the used garment is shown in a rolled condition for disposal according to this embodiment of the invention. The hook tabs 28 and loop patch 21 components which were used in the primary fastening means to releasably fasten the waistbands 16 and 17 together about the torso of the wearer are no longer used for this mode of disposal. The garment is disposed of after it is used by folding or rolling it longitudinally from the front waistband 17 towards rear waistband 16. The lateral ears 25 and 26 are then folded inwardly (toward the center L) and tabs 52 and 53 extended to draw the package taut. As shown on FIG. 13, the hooks 28 extend away from the rolled garment and adhesive areas 54 of the tabs 52 and 53 are adhered to the outer surface on the plastic backsheet 10. The rolled diaper places the disposability zone for attaching the adhesive in the rear half of the diaper, i.e. the longitudinal one-half of portion including rear waistband 16.

A preferred example of the absorbent article of this fourth embodiment of the invention is a disposable diaper, such as shown on FIGS. 9–13. The dimensions for the components of the primary and secondary fastening means are the following:

| Part Name | No. | Range Width | Range Length | Preferred Dimensions For Medium Diaper Width | Length |
|---|---|---|---|---|---|
| Loop Patch | 21 | .5–5 in. | 4–14 in. | 1.75 in. | 9 in. |
| Fastening Tape | 27 | .25–4 in. | 1–6 in. | 1 in. | 3 in. |
| Hook Material | 28 | .25–4 in. | .1–4 in. | 1 in. | .5 in. |
| Pres. Adhesive Area | 54 | .25–4 in. | up to 3 in. | 1.0 in. | .62 in. |
| Finger Tab | 30 | .25–4 in. | 0 to .5 in. | 1.0 in. | .19 in. |

FIFTH EMBODIMENT

Another embodiment of the invention is shown on FIGS. 14–18 in which another mechanical form of secondary fastening means is utilized to secure the rolled garment for disposal after use.

Figure 14:
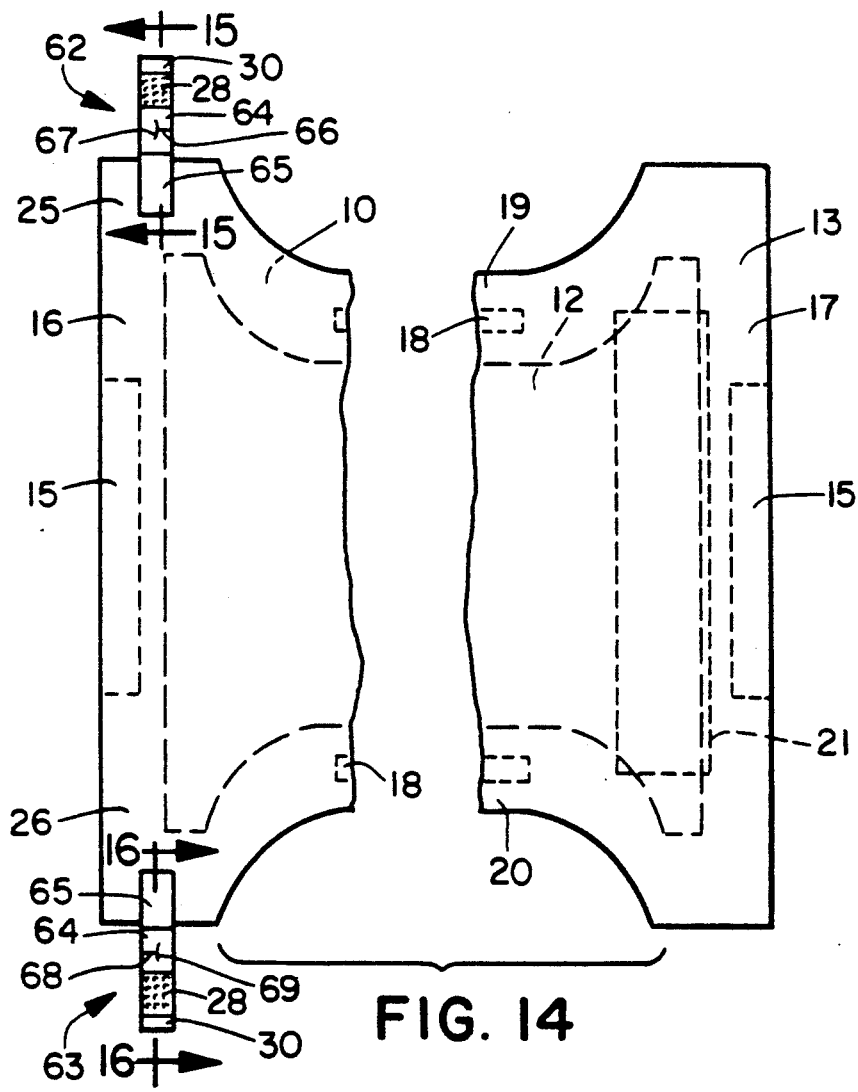
FIG. 14 is a fragmented top plan view, broken away, of a disposal diaper constructed according to a fifth embodiment of the invention.
Figure 15:
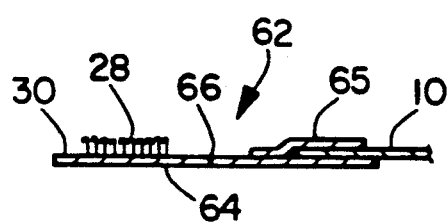
FIG. 15 is a sectional view taken along line 15—15 on FIG. 14.
Figure 16:
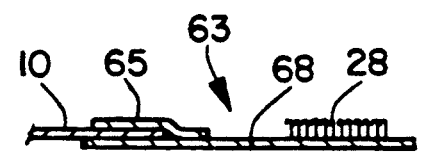
FIG. 16 is a sectional view taken along line 16—16 on FIG. 14.

On FIG. 14, the absorbent article is shown as a disposable diaper with the middle portion broken away for ease of illustration. The article includes a liquid impermeable backsheet 10 and liquid permeable topsheet 13. The absorbent body 11 is shrouded by a tissue wrap 12 and placed between sheets 10 and 13 which are adhesively attached to each other to form the composite in the manner disclosed FIGS. 1–3. Loop material is placed at front waistband 17 as a patch 21 of fabric centered on the longitudinal axis and adhesively bonded onto the outer surface of backsheet 10, as earlier described herein. Attachment tabs 62 and 63 are constructed and attached to the ear portions of the article along the outer margins at the rear waistband 16. The tabs 62 and 63 are each constructed of a relatively heavy and rigid substrate tape 64 (FIGS. 15 and 16), such as a 2.0 mil polypropylene. The substrate 64 is adhesively bonded onto the outer surface of the backsheet 10 by hot melt adhesive of the type disclosed earlier herein. A second tape 65 is overlaid on the inside surface of backsheet 10 and adhesively attached at its extreme end onto the surface of substrate tape 64 and the balance is adhered onto the inside surface of either the backsheet 10 or the composite layers of the ear portion where the tab is affixed. (FIGS. 15 and 16). Hook material 28 is attached to the inside face of tape 64 by adhesive, such as National 70-3016 hot melt adhesive, placing the hook portions on tabs 62 and 63 near the outboard end of the tape 64. The hook material may be, for example, Velcro hook style 15 made of Ferro polypropylene 9004N, as previously described. The outer portion of the substrate provides a finger tab 30 for releasing the hook-loop fastener. In use, the ears 25 and 26 overlie the front waistband 17 of the garment. Tabs 62 and 63 are pressed onto the loop material patch 21 securing the diaper about the waist of the wearer. This comprises the primary fastening of the diaper.

Figure 18:
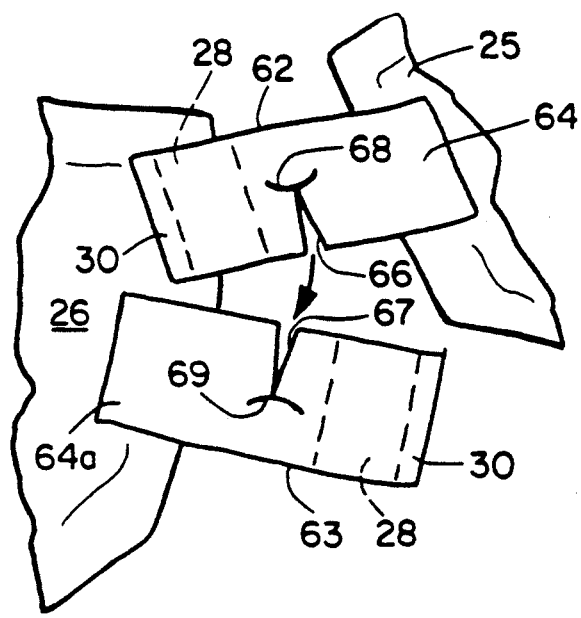
FIG. 18 is an enlarged partial perspective view of the diaper of FIG. 17 illustrating the slotted tabs being placed in their locked position for securing the rolled diaper for disposal.
Figure 17:
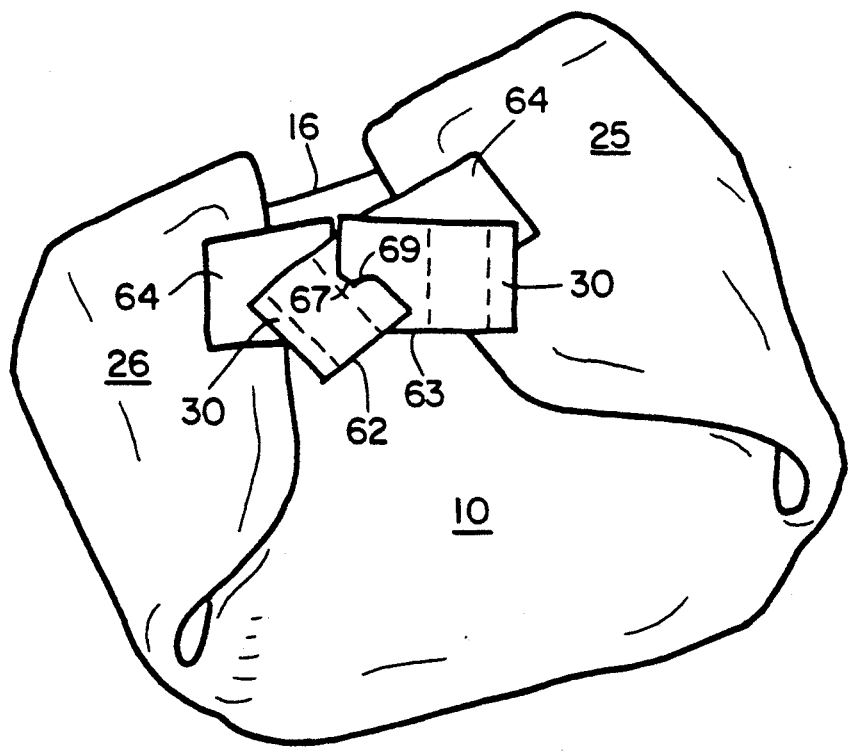
FIG. 17 is a perspective view of the diaper of FIG. 14 folded and fastened by slotted tabs on the ends of the rear waistband which are interlocked securing the diaper for disposal.

The secondary fastening means of the diaper for its disposal comprises a mechanical fastener. Tape 64, 64a of the tabs 62 and 63 are provided with a pair of interlocking slot fastener means between the hook tab portion 28 and the edge of the ear portion of the diaper. The tab 62 has a lateral slot 66 extending partially across the tape 64 and is flared angularly at 68 extending in opposite directions along the tape to provide a first Y-shaped slot element. The width of slot 66 is substantially the same as the thickness of tape 64. Similarly, tab 63 has a transverse slot 67, cut partially across tape 64a but from its opposite side edge in relation to the slot 66 of tab 62. The bottom of slot 67 has the oppositely flared angular ends 69 to form the second Y-shaped slot element. The Y-shaped slots 66,68 and 67,69 face in opposite longitudinal directions of the garment (FIG. 14). Referring to FIGS. 17 and 18, the garment is disposed of after use by folding or rolling it from the front waistband 17 toward rear waistband 16. The opposite ears 25 and 26 of the diaper are folded inwardly toward each other placing the opening of the slots 66 and 67 opposite each other. By somewhat flexing the tab in arcuate form, the slots open up at the end (shown exaggerated on FIG. 18) for ease of interlocking them. The tabs 62 and 63 are brought together to engage the Y-shaped slots in each other to straddle the tapes until seated in the manner shown on FIG. 17. The flared interior roots 68 and 69 of the two Y-shaped slots 66 and 67 interengage along the slot perimeter to lock the tabs 62 and 63 together. This provides a secondary fastening means for retaining the rolled, used garment for disposal.

In conjunction with the several embodiments of the invention described herein, FIGS. 19-22 show various techniques and attachments for fastening the tape tabs to the ear portion of the garment.

Figure 19:
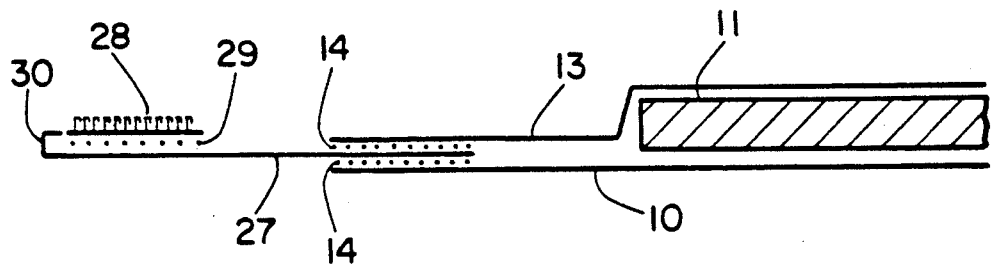
FIG. 19-22 are sectional views (partially schematic) of the diaper ear portion illustrating several lamination constructions for the fastener tabs with the diaper.

FIG. 19 illustrates the lamination of the tape between the topsheet 13 and backsheet 10 at the margin of the ear portion. The construction shown on FIG. 19 was earlier described, for example, in connection with the description of the first and fourth embodiments (FIGS. 1-4 and 9-11). Other tab attachment structures are shown on FIGS. 20-22.

Figure 20:
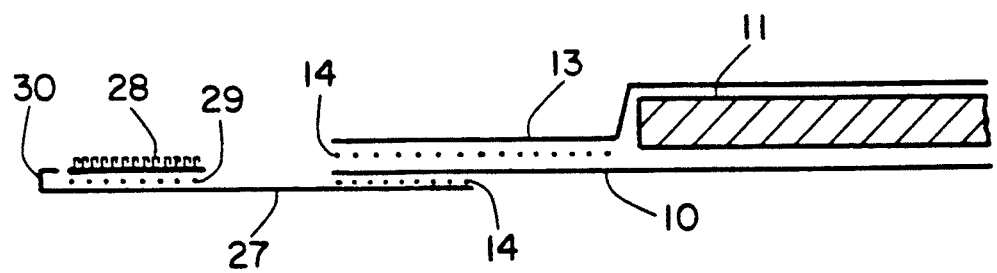

Referring to FIG. 20, the tape 27 of the attachment tab is adhesively attached by an adhesive layer 14 (represented by dot pattern) onto backsheet 10 and the backsheet and topsheet 13 are laminated by a similar adhesive layer 14 in the ear portions of the garment. The hook tab material 28 is adhesively attached to the film substrate of tape 27 by adhesive layer at 29.

Figure 21:
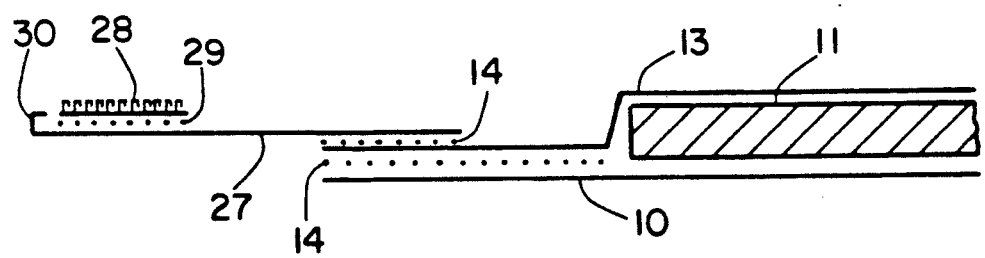

As shown on FIG. 21, another form of attachment of the tabs is shown. The tape 27 is adhesively attached to the topsheet 1 by the adhesive layer 14 and the topsheet is adhesively attached to the backsheet 13. Hook tab material 28 is connected to the film substrate 27 by adhesive at 29.

Figure 22:
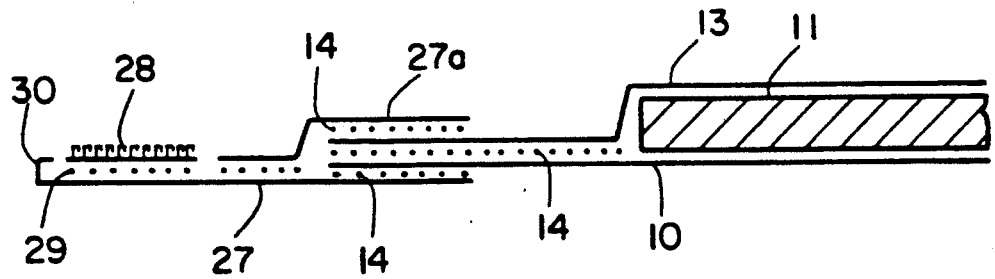

And, as seen on FIG. 22, the attachment tab 27 may be connected to the ear portion of the garment by adhesively attaching the topsheet 13 and backsheet 10 together, and straddling the laminate 13,10 with a tape segment 27a adhered onto the tape substrate of tab 27 and onto topsheet 13 extending inboard of its marginal edge. The hook material of tab 28 is fastened in the same way, as previously described, by hot melt adhesive layer 29.

In the disclosure, the elements are disclosed as being attached by adhesives, as the preferred examples for connecting the various fastener elements to the sheets and tapes of the article. It should be understood these attachments may be made by sonic welding, ultrasonic techniques, heat bonding (where applicable) or other known means of attachment.

In selecting a style of mounting the attachment tab 27 onto the article, certain trade-offs are available comparing security or strength of the attachment versus cost in adhesives, material and manufacturing cost of application.

In connection with the embodiments described herein and within the concept of the invention, the hook and loop mechanical fastener can be replaced with other mechanical fastening systems (not shown), such as buttons, hooks, hook and eye fasteners, snaps, or the like; cooperating with corresponding buttonholes, eye receivers, snap receivers or the like. While the representative embodiments of the invention described above include specific locations for the hook components and the loop components of the fastening systems, it is readily apparent that the relative locations of the hook and loop components may be reversed or exchanged for each other. In optional arrangements, a hook component may be substituted for the described loop component, and a loop component may be substituted for the described hook component to produce an alternative, operative configuration.

Having described in detail various embodiments including the best mode contemplated for carrying out the invention, it will be readily apparent to those skilled in the art that various changes and modifications may be made without departing from the scope of the invention, as set forth in the appended claims.

It is claimed:

1. A disposable absorbent article, comprising:
superimposed backsheet, absorbent body, and topsheet elements formed to provide a composite;
opposite longitudinal end portions of said composite providing first and second waistband portions, respectively, which are configured to overlap each other near lateral ends thereof upon encircling an abdomen of a user to hold said article on the user, said first waistband portion located in a first half-portion of said composite;
primary mechanical fastening means for securing said first and second waistband portions to each other in said overlapping relationship, said primary mechanical fastening means having a first component attached to said composite on an ear portion at each lateral end of said first waistband portion facing inwardly of said article and having a second component attached to said composite at said second waistband portion, said second component constructed to cooperatively interengage said first components and releasably fasten thereto; and
secondary mechanical fastening means for securing the composite in a disposal condition after use, said secondary mechanical fastening means including an outwardly facing third component overlying said composite in said first half-portion thereof, said third component constructed to mechanically engage each of said laterally positioned first components to secure the composite in the disposal condition with each of said first components overlying said third component.

2. The absorbent article of claim 1 in which the mechanical fastener means comprises:
a hook and loop fastener comprising two interlocking materials, one being a hook material and other being a loop material;
one of said two materials being attached to the lateral end portions of the first said waistband portion and another of said two materials being attached to said second waistband portion, the said materials being engageable to attach the first and second waistband portions to each other.

3. The absorbent article of claim 2 in which the hook material is attached on the first waistband portion by laterally extending tabs and a patch of the loop material is attached on the second waistband portion by adhesive.

4. The absorbent article of claim 3 in which the secondary fastening means comprises a second patch of loop material attached on the backsheet surface of the composite in the said longitudinal one-half portion thereof common with said tabs, whereby engaging the hook material of at least one of the tabs with said second patch of loop material secures the article in said condition for disposal.

5. An absorbent article as recited in claim 1, wherein said first component is a polymeric, hook style material having a flexural modulus of 70,000-120,000 psi and a Shore hardness within a range of about D-40 to D-80.

6. An absorbent article as recited in claim 5, wherein said second component is a two bar, warp knit fabric having courses in a range of 21-41 per inch and having wales in a range of 26-46 per inch.

7. An absorbent article as recited in claim 6, wherein said Shore hardness is about D-61.

8. An absorbent article as recited in claim 6, wherein said fabric has a caliper within a range of about 0.01 to 0.04 inch and basis weight within a range of about 1.0-3.0 ounces per square yard.

9. An absorbent article as recited in claim 6, wherein said hook style material comprises J-shaped hooks arranged with a hook density of 440-1040 hooks per square inch.

10. An absorbent article as recited in claim 9, wherein said hooks have a row density within a range of about 20-60 rows per lineal inch of width.

11. A disposable absorbent article, comprising:
an absorbent body of selected shape disposed between a backsheet which is substantially impermeable to liquid and a topsheet which is substantially permeable to liquid and will contact a wearer's skin, said backsheet and topsheet being attached to each other to provide a sheet composite having a first longitudinal end and a second longitudinal end, said longitudinal ends providing waistband portions for encircling a body of a user to hold said article on the wearer, and said first longitudinal end located in a first longitudinal half-portion of said article;
primary fastening means for releasably securing said waistband portions to each other, comprising a hook-and-loop type fastener having first and second components, and
a tab fixedly connected to said sheet composite at each lateral margin of said first longitudinal end of said sheet composite, each tab having a section of said first component attached thereto facing inwardly of said article, said second component being attached to said sheet composite near said second longitudinal end thereof; and
secondary fastening means for securing the article in rolled or folded condition after use, in which said first component of the first fastening means is engageable with another, outwardly facing compatible fastening component, said other component fixedly attached to the backsheet within said first longitudinal one-half portion of the article and centered on a longitudinal axis thereof, and said other component constructed to mechanically engage each of said laterally positioned first components at the same time when the article is in the rolled or folded condition after use with each of said first components overlying said other component.

12. An absorbent article as recited in claim 11 wherein said first component is a polymeric, hook style material having a flexural modulus of 70,000-120,000 psi and a Shore hardness within a range of about D-40 to D-80, and wherein said second component is a two bar, warp knit fabric having courses in a range of 21-41 per inch and having wales in a range of 26-46 per inch.

13. An absorbent article as recited in claim 12, wherein said fabric has a caliper within a range of about 0.01 to 0.04 inch.

14. An absorbent article as recited in claim 12, wherein said fabric has a caliper within a range of about 0.01 to 0.04 inch and basis weight within a range of about 1.0-3.0 ounces per square yard.

15. An absorbent article as recited in claim 12, wherein said Shore hardness is about D-61.

16. An absorbent article as recited in claim 12, wherein said hook style material comprises J-shaped hooks arranged with a hook density of 440-1040 hooks per square inch.

17. An absorbent article as recited in claim 16, wherein said hooks have a row density within a range of about 20-60 rows per lineal inch of width.

18. A disposable absorbent article, comprising:
superimposed backsheet, absorbent body and topsheet elements formed to provide a composite;
opposite longitudinal end portions of said composite providing first and second waistband portions, respectively, which are configured to overlap each other near ends thereof upon encircling an abdomen of a user, said first waistband portion located in a first half-portion of said composite;
primary mechanical fastening means for securing said first and second waistband portions to each other in said overlapping relationship, said primary mechanical fastening means having a first component attached to said composite at each lateral end of said first waistband portion and having a second component attached to said composite at said second waistband portion, said second component constructed to cooperatively interengage said first component and releasably fasten thereto;
said first component comprising a hook material having a polymeric base material of about 0.008-0.01 inch thickness having a flexural modulus of about 70,000 to 120,000 psi, a Shore hardness of about D040-D80, and the hook configurations thereof being tapered base to tip, and having a caliper in the range of about 0.035 to 0.050 inch;

said second component comprising a loop material composed of a knit fabric having a raised and stabilized loop construction and a basis weight in the range of about 1.0-3.0 oz per square yard, said fabric including fabric yarns in which about 15%-35% of the fabric yarns are yarns having 1-15 filaments per yarn and having a yarn denier within the range of about 15-30d, and in which about 65%-85% of the fabric yarn are yarns having about 10-30 filaments per yarn and a yarn denier within the range of about 30-50d; and secondary mechanical fastening means for securing the composite in a disposal condition after use, said secondary mechanical fastening means including a third component overlying said composite in said first half-portion thereof, said third component constructed to mechanically engage each of said laterally positioned first components when the composite is in the disposal condition with each of said first components overlying said third component, and said first and third components having a minimum shear property of 200 gm per square inch and a minimum peel property of 75 grams per inch of width.

19. An article as recited in claim 18, wherein said hook material has an alternating hook design.

20. An article as recited in claim 18, wherein said hook material has a hook density within a range of about 440 to 1040 hooks per square inch.

21. An article as recited in claim 18, wherein said hook material has a hook density of about 740 hooks per square inch.

22. An article as recited in claim 18, wherein said hook material has a row density within a range of about 20-60 rows to the lineal inch of width.

23. An article as recited in claim 18, wherein said hook material has a row density of about 40 rows to the lineal inch of width.

24. An article as recited in claim 18, wherein said loop material comprises a two bar warp knit fabric having courses in a range of 21-41 per inch and having wales in a range of 26-46 per inch.

25. An article as recited in claim 24, wherein said loop material has a caliper within a range of about 0.01 to 0.04 inch.

26. An article as recited in claim 25, wherein said loop material has a basis weight within a range of about 1.0-3.0 ounces per square yard.

* * * * *

UNITED STATES PATENT AND TRADEMARK OFFICE
CERTIFICATE OF CORRECTION

PATENT NO. : 5,176,671

DATED : January 5, 1993

INVENTOR(S) : Thomas H. Roessler, Bruce M. Siebers, Robert L. Popp, Charles R. Fallen It is certified that error appears in the above-identified patent and that said Letters Patent is hereby corrected as shown below:

Column 13, line 65, delete "1" and substitute therefor -- 13 --.

Signed and Sealed this

Sixth Day of September, 1994

Attest:

BRUCE LEHMAN

*Attesting Officer*     *Commissioner of Patents and Trademarks*